United States Patent
Wieder

(10) Patent No.: US 11,098,339 B2
(45) Date of Patent: Aug. 24, 2021

(54) METHODS FOR TESTING ENZYME BASED ELECTROCHEMICAL SENSORS

(71) Applicant: Roche Diabetes Care, Inc., Indianapolis, IN (US)

(72) Inventor: Herbert Wieder, Lampertheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 145 days.

(21) Appl. No.: 16/326,785

(22) PCT Filed: Jul. 4, 2017

(86) PCT No.: PCT/EP2017/066656
§ 371 (c)(1),
(2) Date: Feb. 20, 2019

(87) PCT Pub. No.: WO2018/046160
PCT Pub. Date: Mar. 15, 2018

(65) Prior Publication Data
US 2019/0177764 A1 Jun. 13, 2019

(30) Foreign Application Priority Data
Sep. 7, 2016 (EP) .................................... 16187698

(51) Int. Cl.
*G01N 27/327* (2006.01)
*C12Q 1/00* (2006.01)

(52) U.S. Cl.
CPC .............. *C12Q 1/006* (2013.01); *C12Q 1/001* (2013.01); *G01N 27/3274* (2013.01)

(58) Field of Classification Search
CPC ............. G01N 27/327; G01N 27/3271; G01N 27/3273; G01N 27/3274
See application file for complete search history.

(56) References Cited

U.S. PATENT DOCUMENTS 5,250,419 A 10/1993 Dominique et al.
5,804,048 A * 9/1998 Wong .................... C12Q 1/002
204/403.09
(Continued)

FOREIGN PATENT DOCUMENTS

AU 2015 258 265 A1 12/2015
WO WO 2006/109279 A2 10/2006

OTHER PUBLICATIONS

Emel Emregul et al: "Immobilization of Glucose Oxidase onto Gelatin for Biosensor COnstruction", Journal of Biomaterials Science; Polymer Edition, vol. 16, No. 4; Jan. 1, 2005; pp. 505-519.
(Continued)

*Primary Examiner* — Alexander S Noguerola
(74) *Attorney, Agent, or Firm* — Woodard, Emhardt, Henry, Reeves & Wagner, LLP

(57) ABSTRACT

A method for testing enzyme based electrochemical sensors wherein an electrochemical sensor is provided. A measurement setup is provided, which is operatively coupled to the electrochemical sensor, providing an output signal Z, e.g. a measured signal current, of the electrochemical sensor; and the electrochemical sensor is suitably contacted with a test solution comprising a certain concentration of the primary analyte. The electrochemical sensor is subjected to a certain swept range of temperatures T; an output signal Z is measured for different temperature values T; a derivative Z' of the output signal Z as a function of temperature T, or inverse temperature 1/T, is determined; and a relative derivate Z'/Z at a temperature T, or inverse temperature 1/T, is determined as the ratio between derivative Z' and output signal Z.

13 Claims, 6 Drawing Sheets

(56) References Cited

U.S. PATENT DOCUMENTS

2009/0023222 A1* 1/2009 Wu ................... G01N 27/26
436/95
2009/0156920 A1 6/2009 Kotzan et al.
2011/0297557 A1* 12/2011 Wu .................. G01N 27/4163
205/792

OTHER PUBLICATIONS

Fortier G et al:"Optimization of a Polypyrrole Glucose Oxidase Biosensor", Biosensors and Bioelectronics, Elsevier BV, NL, vol. 5, No. 6; Jan. 1, 1990; pp. 473-490.
Jadan Felipe et al: "Selective Determination of Lysine in Dry-Cured Meats Using a Sensor Based on Lysine-[alpha]-Oxidase Immobilised on a Nylon Membrane", Food Analytical Methods, Springer New York, LLC, US vol. 9, No. 9, 16; Feb. 2016; pp. 2484-2490.

* cited by examiner

(a)

(b)

(c)

(a)

(b)

(a)

(b)

(a)

(b)

METHODS FOR TESTING ENZYME BASED ELECTROCHEMICAL SENSORS

FIELD OF THE INVENTION

The invention relates to methods for testing enzyme based electrochemical sensors for quantitative detection of analytes in aqueous solutions, particularly implantable sensors for detecting analytes in body fluids.

BACKGROUND OF THE INVENTION

Implantable electrochemical sensors are useful tools for the continuous in-vivo monitoring of biological analytes in body fluids, such as blood or interstitial fluid. In one class of such sensors, a primary analyte is continuously reacted in a suitable enzyme catalysed reaction, producing a secondary analyte, which is then electrochemically detected with an amperometric detection setup. Particularly useful are such sensors for continuously monitoring the concentration of glucose in the interstitial fluid of patients with diabetes mellitus.

US 2009/0156920 A1, the disclosure of which is hereby included by reference in its entirety, discloses an advantageous implantable glucose sensor. The sensor comprises a working electrode, a reference electrode and a counter electrode. All electrodes are arranged on an oblong sensor shaft, to be placed in the tissue of a patient. Both the counter electrode and the reference electrode can be realized as Ag/AgCl electrodes. All three electrodes are covered by a semi-permeable membrane.

The working electrode 1, a schematic cross-section of which is shown in the in FIG. 1, comprises a detecting layer 4 consisting of an insoluble matrix of graphite and manganese dioxide particles and an abundant amount of immobilized glucose oxidase (GOx) enzyme. The working electrode, the counter electrode and the reference electrode are covered by a semi-permeable hydrophilised polyurethane membrane 5. The membrane is permeable for water, oxygen and smaller ions present in the body fluid 6 electrolyte, but impermeable for glucose oxidase and other potentially physiologically harmful compounds on the electrodes. The membrane 5 provides only a restricted permeability for the primary analyte glucose, in order to decrease the ratio between glucose concentration and oxygen concentration at the surface of the working electrode, compared to the ratio in the body fluid 6.

At the surface 4a of the detecting layer 4, glucose oxidase catalyses a redox reaction in which in a first step the primary analyte glucose is oxidised to gluconolactone, while in a second step oxygen is reduced to the secondary analyte hydrogen peroxide. With the parameters properly set, and the enzyme catalysed reaction being diffusion-limited, the rate of forming hydrogen peroxide is proportional to the glucose concentration in the body fluid 6. The forming hydrogen peroxide is electrochemically oxidised to oxygen by the manganese dioxide, and thus continuously consumed. The resulting electrons are transferred from the manganese dioxide to the conductive graphite particles, which form an electrical connection to a conducting layer 3.

Using a potentiostat setup, the resulting current between the working electrode and the counter electrode is measured, while the potential between working electrode and reference electrode is actively kept constant at a predefined value. The output signal in the form of the measured signal current is proportional to the rate of continuously forming hydrogen peroxide, and thus also to the glucose concentration in the body fluid.

WO2008/042625 A2, WO 2010/028708 A1 and WO 2014/001382 A1, the disclosure of which is hereby included by reference in its entirety, disclose further embodiments of such sensors, including other examples of used enzymes, charge mediators, and membranes.

Glucose sensors as described above are generally configured such that they are diffusion controlled. This means that all involved reactions and processes, including the enzymatically catalysed oxidation of glucose, are much quicker than the rate of transport of the relevant reactant, here glucose, to the reaction site at the enzyme through the reaction medium, here essentially the semi-permeable membrane 5. The reaction rate is limited by the rate of the slowest, rate determining step, which in the given case is the diffusion of glucose through the semi-permeable membrane. The required behaviour of the sensor can be achieved by providing the enzyme GOx in abundance, while at the same time setting the diffusion rate at a certain level by a using a suitable combination of membrane thickness and permeability.

Malfunctions of medical devices such as the glucose sensors described above may have a considerably negative impact on the health of their users. Erroneous results of measurements may for example lead to potentially harmful therapeutic decisions, or to improper operation of other medical devices using such data, such as e.g. infusion pumps. A measured blood glucose concentration that is higher than the real value may for example cause a user to inject a certain bolus of insulin, in order to avoid a hyperglycaemic situation. In combination with the actually lower real blood glucose concentration, this unnecessarily administrated insulin dose may then lead to a dangerous hypoglycaemic episode. A measured blood glucose concentration that is lower than the real value, on the other hand, will lead to a hyperglycaemic state that causes long term damages.

Therefore, quality control of such sensors is of upmost importance. This includes quality control during and after manufacture, as well as long-term storage stability monitoring, and studying the behaviour of sensors during the intended use. One essential parameter to be tested and monitored is the amount of active enzyme that catalyses the reaction of the primary analyte, since a too low amount of enzyme may lead to too low glucose readings.

However, the enzyme activity in a properly diffusion-controlled sensor is normally hidden behind the rate determining diffusion process.

In one known test method, the enzyme of the detecting layer of the working electrode of a sensor to be examined is isolated, and the amount of enzyme is determined. However, since the enzyme molecules are embedded in a dried, insoluble matrix of manganese dioxide and carbon, covered by a polymer membrane, and the working electrode as such is very small, such a process is difficult. Furthermore, the found amount of active enzyme is not necessarily identical to the amount of active enzyme actually accessible on the surface of the detecting layer. Most of the enzyme molecules in the matrix are not accessible by the analyte, and thus do not contribute to the function of the sensor. Measuring the enzyme content is therefore in most cases an unsuitable analytical method for this class of sensors.

For assessing long-term storage stability, it is a common approach to observe a beginning reaction-controlled behaviour of a sensor. Complex biological compounds such as enzymes are thermodynamically less stable than small molecules, particularly in aqueous solutions, but also in the dry state, and inevitably deteriorate over time. This inherent thermodynamic instability of enzymes restricts the shelf life time of the shown sensors. The decay rate of the amount of active enzyme in a sensor can be determined by the point in time where the amount of active enzyme is no longer sufficient to provide a reaction rate that is higher than the diffusion rate, and the sensor begins to act reaction-controlled instead of diffusion-controlled.

For a reduction of the overall testing times, sensors can be stored at increased temperatures, which increases the thermal deterioration rate. However, for the above-mentioned class of sensors, this approach has the disadvantage that the increased temperature has also effects on the permeability of the membrane. Changes of permeability of the used hydrophilised polyurethane membrane under such conditions actually dominate the change in sensitivity over storage time, again hiding the effect of a reduced enzyme activity.

For actually testing the behaviour of a sensor after a certain storage time, the decrease of enzyme activity is assessed under operating conditions, by observing the decrease of sensitivity (ratio between measured signal and given analyte concentration) over time (so called negative drift), or the change in the curvature of the measured signal as a function of the analyte concentration over time. Such functionality tests have to be carried out over several days.

As explained above, with the known methods a change of the sensor behaviour from diffusion control to reaction control may only be observed with real time measurements over the complete service time period (weeks), after different time periods of storage under normal storage conditions. Thus, enzyme activity measurements are currently very time consuming and demanding in resources, and may deliver results of limited precision.

Tests of the functionality of sensors before releasing batches of manufactured sensors are carried out shortly after manufacture. At that time enzyme activity is still at the original high level, and membrane permeability is unchanged. Under such conditions, enzyme activity is factually not accessible for measurements.

Therefore there is a general need for improvement of test methods for the above-mentioned class of enzyme-based electrochemical sensors.

SUMMARY OF THE INVENTION

It is the overall objective of the present invention to provide advantageous methods for testing enzyme based electrochemical sensors.

These and other objects are substantially achieved by a method according to the independent claim. Further advantageous embodiments follow from the dependent claims and the description.

The present invention may comprise one or more of the features recited in the attached claims, and/or one or more of the following features and combinations thereof.

In a method according to the invention for testing enzyme based electrochemical sensors for quantitative detection of analytes in aqueous solutions, an electrochemical sensor is provided, with a working electrode and a counter electrode. The working electrode comprises an electrical conductor, a solid-state matrix being electrically connected with said conductor and containing an immobilized enzyme able to catalytically convert a primary analyte into a secondary analyte that can be oxidised or reduced when a suitable potential is applied at the working electrode, and a membrane covering said matrix and separating it from the outside. Said membrane is permeable for the primary analyte, such that primary analyte molecules present in an aqueous solution with which the working electrode is contacted can pass through the membrane to the matrix, where they can be catalytically converted into second analyte molecules. A measurement setup is provided, which is operatively coupled to the electrochemical sensor, providing an output signal Z, e.g. a measured signal current, of the electrochemical sensor. The electrochemical sensor is suitably contacted with, e.g. immersed into, a test solution comprising a certain concentration of the primary analyte. The electrochemical sensor is subjected to a certain temperature T, wherein this temperature is swept within a certain range, and an output signal Z is measured for different temperature values T. A derivative $Z'$ of the output signal Z as a function of temperature T, or inverse temperature $1/T$, is determined; and a relative derivate $Z'/Z$ at a certain temperature T, or inverse temperature $1/T$, is determined as the ratio between derivative $Z'$ and output signal Z.

In an advantageous variant of such a method according to the invention, an offset function $Z_{offset}$, for example a constant offset, is subtracted from output signal Z prior to using output signal Z for determining the derivative $Z'$. In a particular advantageous variant, the offset function $Z_{offset}$ is determined in an iterative process with at least one iteration round, said iterative process comprising the assessment of a derivative $Z'$ and/or relative derivative $Z'/Z$ obtained using a certain offset function, e.g. the deviation of the derivative and/or relative derivative from a certain model function, and determining changes in the offset function based on said assessment of the derivative and/or relative derivative.

In a method according to the invention, advantageously the enzyme is glucose oxidase, the primary analyte is D-glucose, and the secondary analyte is hydrogen peroxide.

Advantageously, in a method according to the invention the temperature is increased or decreased stepwise.

In a method according to the invention, the temperature is advantageously swept in a certain range, e.g. between 2° C. and 42° C. The limits of lower and upper temperature are given by the operative conditions necessary for carrying out measurements. Measurements are not possible below the freezing point of water, and at temperatures close to 0° C., the increasing viscosity of the aqueous solutions starts to become relevant. Above a certain temperature range, enzymes start to denaturate, particularly in an aqueous environment. Depending on the setup, a temperature sweep may also begin e.g. at 0.5° C. or 1° C., or at higher temperatures, e.g. 5° C., or 10° C. The upper sweep limit may be set to a lower value, e.g. 37° C. or 40° C., or the sweep may end at 45° C.

In another advantageous variant of the discussed methods according to the invention, the applied temperature is modulated with a certain offset temperature, frequency and amplitude, resulting in a modulated output signal with an offset and modulation amplitude; and the relative derivative $Z'/Z$ is determined as the quotient of output signal modulation amplitude and output signal offset.

In a further advantageous variant of the discussed methods according to the invention, the obtained relative derivate $Z'/Z$ values are compared to given calibration data sets corresponding to sensors comprising certain amounts of active enzyme.

In another advantageous variant of the discussed methods according to the invention, based on the obtained relative derivate $Z'/Z$ values a temperature shift is determined as the temperature or inverse temperature where a function fitted to the relative derivate $Z'/Z$ data reaches a certain value. In a particularly advantageous variant of such a method, the determined temperature shift is compared to given calibration data corresponding to sensors comprising certain amounts of active enzyme.

In a further variant of the discussed methods according to the invention, the sensor to be analysed is subjected to a certain treatment prior to carrying out the measurement, e.g. subjecting the sensor to a certain temperature for a certain time period; or subjecting the sensor to operative conditions for a certain time period.

In yet another variant of the discussed methods according to the invention, after carrying out the measurement on the sensor to be analysed, said sensor is subjected to a certain treatment prior to carrying out another measurement, e.g. subjecting the sensor to a certain temperature for a certain time period; or subjecting the sensor to operative conditions for a certain time period.

In yet a further variant of the discussed methods according to the invention, the measurement is carried out with two or more test solutions having different properties, e.g. different concentrations of the primary analyte, different properties of enzyme inhibiting agents, and/or different pH values.

BRIEF DESCRIPTION OF THE DRAWINGS

In order to facilitate the understanding of the present invention, reference is now made to the appended drawings. These references should not be construed as limiting the present invention, but are intended to be exemplary only.

DETAILED DESCRIPTION OF THE INVENTION

The disclosed method for testing enzyme based electrochemical sensors is based on observing the sensitivity of a sensor depending on the temperature, and applying certain analytical steps on the results, in order to obtain information on the enzyme activity under operational conditions.

Kinetic Model

Figure 1:
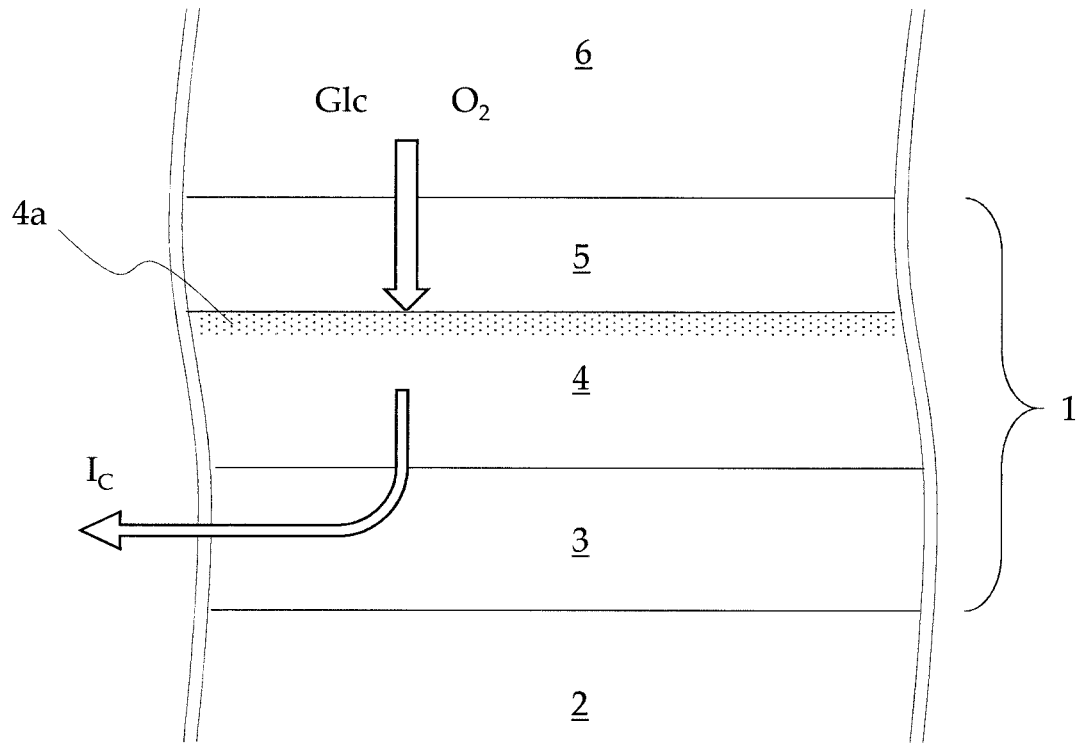
FIG. 1 schematically shows a cross-section through a working electrode of an electrochemical glucose sensor as it is known from the prior art.
Figure 2:
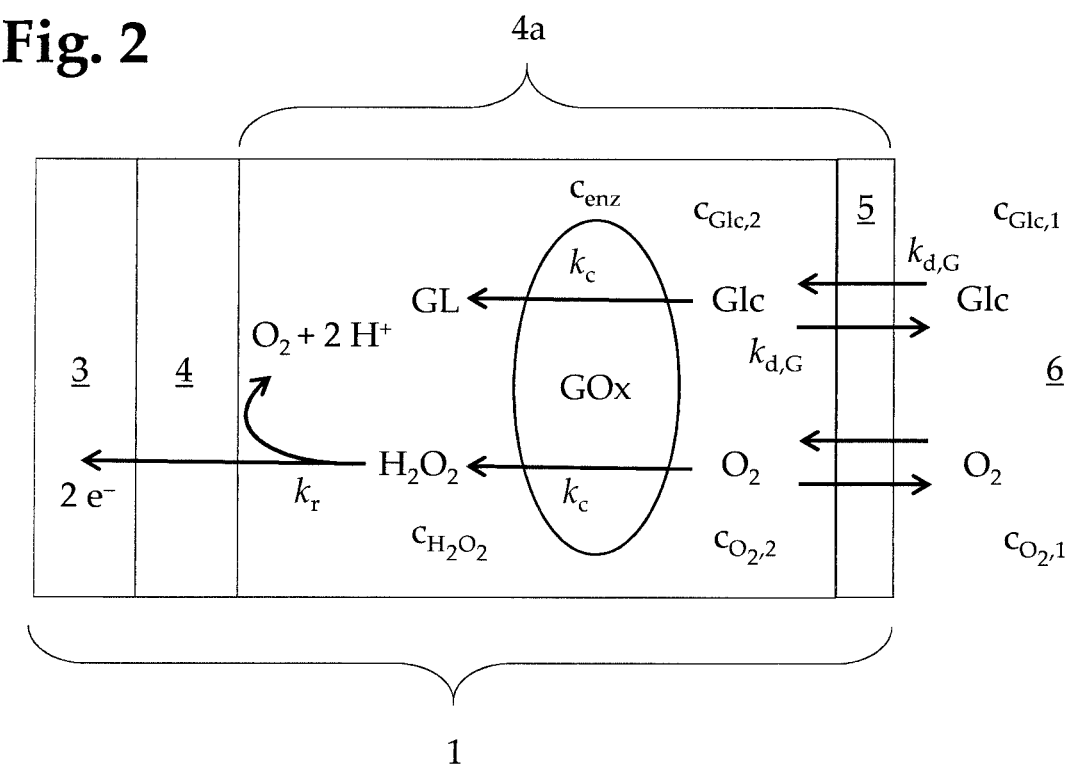
FIG. 2 schematically shows the processes taking place during the detection of glucose with the sensor of FIG. 1.

FIG. 2 schematically shows a mathematical model of the different kinetically relevant chemical processes that take place at a working electrode 1 as shown in FIG. 1, during the detection of glucose.

The sensor is in contact with an analyte solution 6, which for the intended use of the sensor will be a body fluid such as interstitial fluid or blood, or for test purposes a corresponding physiological solution with a known glucose concentration $c_{Glc,1}$. The glucose molecules diffuse across the membrane with a given rate constant $k_d$. The overall rate of diffusion of glucose from the analyte solution 6 to the detecting layer 4, 4a is then proportional to the concentration gradient of glucose across the membrane 5, $\Delta c_{Glc,diff}/\Delta t = k_d c_{Glc,1} - k_d c_{Glc,2} = k_d (c_{Glc,1} - c_{Glc,2})$.

The glucose molecules at the surface area 4a of the detecting layer are continuously oxidised by glucose oxidase molecules, while molecular oxygen is reduced to hydrogen peroxide. The corresponding reaction mechanism and enzyme kinetics are known to the skilled person. The overall rate of production of hydrogen peroxide (the secondary analyte) is a function of the local concentrations of enzyme, oxygen, and glucose (the primary analyte). Since membrane 5 is highly permeable for oxygen, but only permeable at a reduced rate for glucose, the local concentration $c_{O2,2}$ of oxygen at the detection layer is considerably higher than the local glucose concentration $c_{Glc,2}$. The amount of enzyme in the detecting layer is chosen such that under normal operating conditions, the effective concentration of enzyme $c_{enz}$ in the active area is also considerably higher than $c_{Glc,2}$. As a result, the overall rate of hydrogen peroxide production is essentially proportional only to the concentration of Glucose, $\Delta c_{H2O2,cat}/\Delta t = -\Delta c_{Glc,cat}/\Delta t = k_c c_{Glc,2}$, with the effective catalytic reaction rate $k_c$ being a function of $k_{cat}$, $c_{O2,2}$, $c_{enz}$ and $c_{Glc,2}$. As mentioned above, for $c_{enz} \gg c_{Glc,2}$ the catalytic rate $k_c$ will be essentially independent from $c_{enz}$ and $c_{Glc,2}$. For $c_{enz} \ll c_{Glc,2}$ on the other hand $k_c$ will be proportional to $c_{enz}$.

The produced hydrogen peroxide is continuously consumed in the electrochemical reduction reaction, and is oxidised to oxygen, at a redox reaction rate $k_r$. The resulting electrons give rise to a signal current I that is measured with a potentiostat setup. The working potential of the potentiostat setup is set well above the Nernst potential for the electrochemical oxidation of hydrogen peroxide.

The signal current is proportional to the rate of oxidised hydrogen peroxide, and thus to the hydrogen peroxide concentration, $I \, \alpha \Delta c_{H2O2,red}/\Delta t = F(-k_r c_{H2O2})$.

In a steady state equilibrium with $\Delta c_{H2O2,red}/\Delta t + \Delta c_{H2O2,cat}/\Delta t = 0$ and $\Delta c_{Glc,cat}/\Delta t + \Delta c_{Glc,diff}/\Delta t = 0$, the result is a signal current I that is proportional to the primary analyte concentration in the analyte solution $c_{Glc,1}$:

$$I = Bk_r k_c c_{Glc,2} = Bk_r [k_c k_d/(k_c + k_d)] c_{Glc,1}$$

B is a system specific factor. It may vary within a certain range for individual sensors, and among distinct production batches. The sensitivity S of a sensor is defined as $S = I/c_{Glc,1}$, such that $$S = Bk_r k_c k_d/(k_c + k_d)$$

In an operative sensor, the amount of active and accessible GOx enzyme and the properties of the membrane regarding the permeability for glucose will be set in such a way that $k_c \gg k_d$, which simplifies the relation between sensitivity and kinetic rates to $S \cong B \, k_r \, k_d$. Such a sensor is thus essentially diffusion controlled.

In the inventive method, the temperature dependence of the sensitivity S is used to obtain information on the involved kinetic rates, particularly on the effective catalytic reaction rate. The effective catalytic reaction rate comprises valuable information on the actual enzyme activity, which else, as explained further above, would not be accessible, or only at high costs and after very long experiments.

For the purpose of the inventive method, the signal current of a sensor is measured under operative conditions for different temperatures, in the range between 2° C. and 42° C., in which enzyme based electrochemical sensors in aqueous solutions are actually operative. The sensitivity is then determined based on the signal current and the used glucose concentration.

Diffusion rate $k_d$, effective catalytic reaction rate $k_c$, and redox reaction rate $k_r$ are temperature dependent, which in the simplest general case, as for diffusion, may be described by an Arrhenius equation $k_d(T)=k_d^0 \exp(-A_d/T)$. Although the kinetics are more complicated for the catalytic reaction, the temperature dependence of $k_c(T)$ may nevertheless be described by an exponential function similar to an Arrhenius equation. Also $k_r(T)$ can be expected to show such an exponential behaviour.

For small temperature ranges, the temperature dependence may alternatively be described by an exponential function depending on temperature T, as will be explained bellow, instead of the inverse temperature 1/T as in the Arrhenius equation.

Data Analysis

In the following, two approaches for analysing the obtained measurement data are described.

In a first approach, it is assumed that over the comparably small temperature range of 40 K between the operative range between 2° C. and 42° C., the temperature dependency of reaction rates $k_d$ and $k_c$ may be described in approximation by $$k_i(T)=k_i(T_0)p_i^{[(T-T_0)/1K]}.$$

For the following it is assumed that for a sensor as described $p_d \cong 1.03$ and $p_c \cong 1.07$, while scientific literature suggest values of $p_d \cong 1.015\text{-}1.022$. However, as will be shown, said values are actually not directly relevant for assessing the enzyme activity. With the estimated values, the equation above corresponds to an increase of the corresponding reaction rate of approx. 7% per degree Celsius for $k_c$ and approx. 3% per degree Celsius for $k_d$. Of course, in practise such values will depend on the specific chemistry and construction of a certain enzyme based electrochemical sensor system.

The sensitivity $S(T)=B\ k_r(T)\ k_c(T)\ k_d(T)/[k_c(T)+k_d(T)]$ thus can be approximated by $$S(x)=Bk_{r0}p_r^x k_{c0} p_c^x k_d^0 p_d^x /[k_{c0}p_c^x+k_{d0}p_d^x]$$

with $k_{i0}=k_i(T_0)$, and $x=(T-T_0)/1$ K. The derivative $S'(x)=dS(x)/dx$ of $S(x)$ is then $$S'(x)=5\{\ln(p_r p_c p_d)-\ln(p_c)[1+(k_d/k_c)]^{-1}-\ln(p_d)[1+(k_c/k_d)]^{-1}\}$$

This can be simplified to a relative derivative of the sensitivity:

$$\begin{aligned}S'(x)/S &= \ln(p_r p_c p_d) - \ln(p_c)[1 + \exp\{\ln(k_{d0}/k_{c0}) + \ln(p_d/p_c)x\}]^{-1} - \\ &\quad \ln(p_d)[1 + \exp\{\ln(k_{c0}/k_{d0}) + \ln(p_c/p_d)x\}]^{-1} \\ &= \ln(p_r) + \ln(p_c)\ sig(-a - bx) + \ln(p_d)\ sig(a + bx), \\ &= \ln(p_r p_c) - \ln(p_c/p_d)\ sig(a + bx),\end{aligned}$$

respectively $$S'(T)/S=\ln(p_r p_c)-b\,sig(a+b[T-T_0]),$$

with the logistical function $sig(y)=e(y)/[1+\exp(y)]$, $a=\ln(k_{c0}/k_{d0})$, and $b=\ln(p_c/p_d)$.

It should be noted that the relative derivative $S'(T)/S$ of sensitivity $S$ is identical to a corresponding relative derivative $I'(T)/I$ of the signal current $I$ (or any other corresponding output signal $Z$), since $S(T)=I(T)/c_{Glc,1}$. Thus the relative derivative $S'/S$ can directly be obtained from the measured output signal. In the following, all referrals to the relative derivative $S'/S$ of the sensitivity encompass also the identical relative derivative $I'/I$ and $Z'/Z$.

For small signal currents, a Y axis offset due to small residual currents will have a larger perturbing influence on the relative derivative $I'(T)/I$ than for larger current signals, where such an influence is negligible. Thus, advantageously such residual currents are taken into account, in order to avoid systematic errors.

Figure 3:
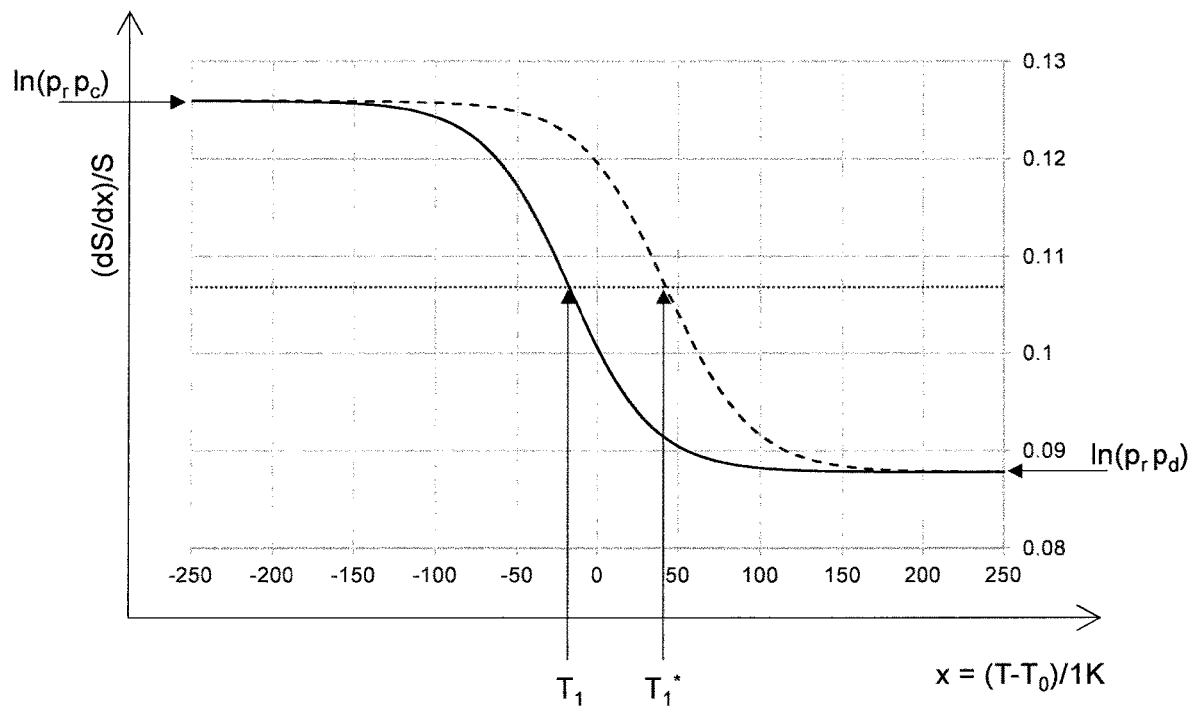
FIG. 3 schematically depicts a model function for the temperature dependence of the relative derivative of the sensor sensitivity.

Such a function $S'(T)/S$ is schematically depicted in FIG. 3 (black line), with parameters $p_r=1.06$; $p_c=1.07$; $p_d=1.03$; $k_{r0}=100$ (arbitrary units); $k_{c0}=10$ (arbitrary units); and $k_{d0}=5$ (arbitrary units). The function shows the transition from the reaction controlled temperature range below $T_1$, where the temperature dependence is essentially governed by the catalytic reaction, $S \cong B\ k_r\ k_c$, to the diffusion controlled temperature range above $T_1$, where the temperature dependence is essentially governed by the diffusion process of glucose, $S \cong B\ k_r\ k_d$. The transition temperature $T_1$ is given by $$T_1=T_0-a/b=T_0-\ln(k_{c0}/k_{d0})/\ln(p_c/p_d)$$

It should be noted that the basic temperature $T_0$ as such is actually irrelevant for the mathematical model, since a change of $T_0$ will be compensated by the corresponding change of $k_{c0}=k_c(T_0)$ and $k_{d0}=k_d(T_0)$.

The gradient $S''/S=(dS^2/dx^2)/S$ of the function $S'(x)/S$ at the transition temperature $T_1$, respectively at $x=0$, is $[(dS^2/dx^2)/S]_{x=0}=-b^2/4=-[\ln(p_c/p_d)]^2/4$, which provided information on the parameters $p_c$ and $p_d$, namely $$p_c/p_d=\exp[2(-[(dS^2/dx^2)/S]_{x=0})^{1/2}].$$

If a sensor has an overall enzyme activity that is reduced, compared to the nominal value, this will lead to a reduced effective catalytic reaction rate constant $k_c^* < k_c$. In a situation where the effective concentration of enzyme is not considerably larger than the concentration of glucose, the effective catalytic reaction rate will start to show a linear dependence on the amount of accessible and catalytically active enzyme as the limiting factor. The temperature dependence of the catalytic reaction, however, will not be influenced, and thus $p_c^*=p_c$.

In the model function $S'(T)/S$ as described above and shown in FIG. 3, a reduced catalytic reaction rate constant $k_c^*$ will lead to a shift of the transition temperature toward higher temperatures, $T_1^*=T_0-\ln(k_{c0}^*/k_{d0})/\ln(p_c/p_d)$, without further changing the function. Such a shifted function is shown in FIG. 3 (dashed line), with $k_{c0}^*=1$ (arbitrary units). The shift of the transition temperature can provide useful information on the relative change in $k_c$:

$$\begin{aligned}\Delta T_1 = T_1^* - T_1 &= -\ln(k_{c0}^*/k_{d0})/\ln(p_c/p_d) + \ln(k_{c0}/k_{d0})/\ln(p_c/p_d) \\ &= -\ln(k_{c0}^*/k_{c0})/\ln(p_c/p_d).\end{aligned}$$

With $k_{c0}*/k_{c0} = k_c*/k_c$, it results $\ln(k_c*/k_c) = -\Delta T_1 \ln(p_c/p_d)$. If now an essentially complete function S'(x)/S could be measured, the difference between the maximum value and the minimum value of would be equal $A(S'/S) = \ln(p_c/p_d)$, resulting in $$k_c*/k_c = \exp[-\Delta T_1 \Delta(S'/S)]$$

Alternatively the gradient at the transition temperature, $[S''/S]_{x=0} = -[\ln(p_c/p_d)]^2/4$ can be used for calculating the relative change of $k_c$, $$k_c*/k_c = \exp(-2\Delta T_1 \{-[S''/S]_{x=0}\}^{1/2}).$$

However, as can be seen in FIG. 3, the sigmoidal function of S'(x) is rather broad for the given parameters, such that in a comparatively small window of about 40 K, in which an enzyme based electrochemical sensor is operative (see further above), one will only have access to a small part of such a function, which will not allow to determine $\ln(p_c/p_d)$ from $[S''/S]_{x=0}$ or $\Delta(S'/S)$. Nevertheless $\Delta T_1$ can be obtained also for such cases. Furthermore it is clear that in any case a determined gradient will be equal or less than the gradient at $T_1$, $[S''/S]_{measured} \geq [S''/S]_{x=0}$, which allows at least a qualitative statement regarding the decreased reaction rate:

$$k_c*/k_c \leq \exp(-2\Delta T_1 \{-[S''/S]_{measured}\}^{1/2})$$

Similar qualitative information can be obtained from the lowest and highest measured value for S'/S:

$$k_c*/k_c \leq \exp[-\Delta T_1 \{(S'/S)_{max} - (S'/S)_{min}\}]$$

Second approach: While the above-mentioned approach for data analysis is based on a mathematical model applying an approximation $k_i(T) = k_i(T_0) p_i^{[(T-T_0)/1\ K]}$ for the reaction rate constants, a similar assessment is possible based on the more accurate Arrhenius equation $k_i(T) = k_i^0 \exp(-\Delta_i/T)$, with $k_i^0$ being a maximum reaction rate for T toward infinity. In this second approach, a relative derivative of the sensitivity is derived as a function of the inverse temperature $T^{-1}$ instead of $x = T - T_0$, $$S'(T^{-1})/S = (-A_r - A_c) - d\,\mathrm{sig}(c + d\,T^{-1}),$$

with the logistical function $\mathrm{sig}(y) = e(y)/[1 + \exp(y)]$, $c = \ln(k_c^0/k_d^0)$, and $d = (-A_c + A_d)$. Similar to the first system model, a shift of the curve $S'(T^{-1})/S$ and its gradient can be utilized for gaining information on the relative change in the effective catalytic reaction rate $k_c^0*/k_d^0$.

Both approaches, which essentially only differ by the x-axis used, either T or 1/T, deliver similar results, since the function 1/T is approximately linear over the used temperature range of 279-315 K, and vice versa. While the first approach is more intuitive in regard to data interpretation, the second approach based on the Arrhenius equation is actually being more accurate.

Experimental Results

Figure 4:
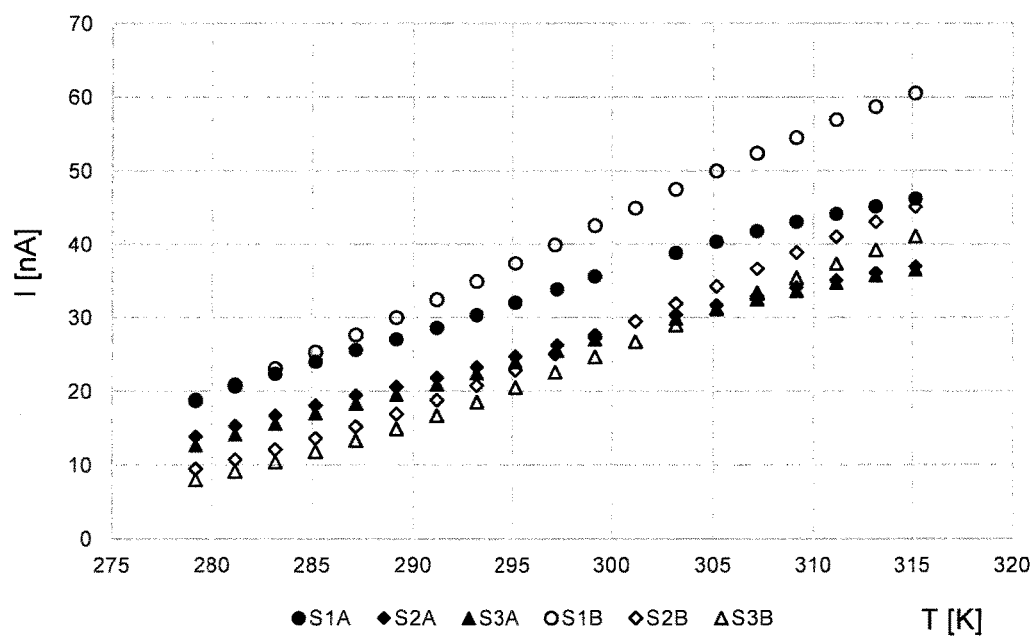
FIG. 4 shows experimental results of measurements of electrochemical glucose sensors, with (a) the signal current I vs. temperature T, (b) the sensitivity S vs. temperature T, and (c) the relative derivative (dS/dT)/S of the sensitivity vs. temperature T.
Figure 4:
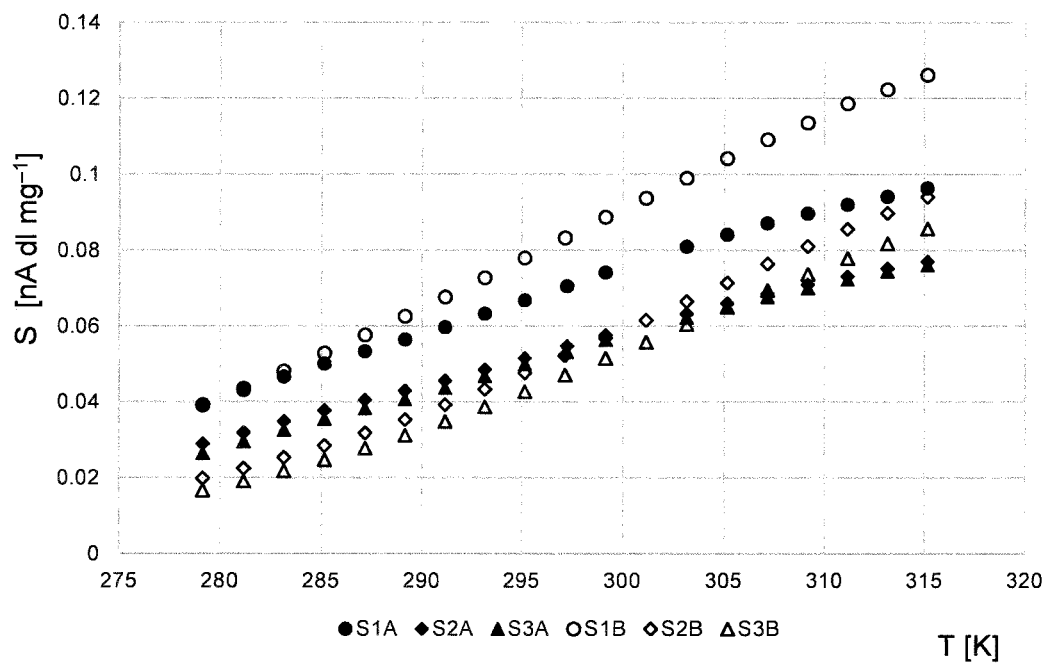
Figure 4:
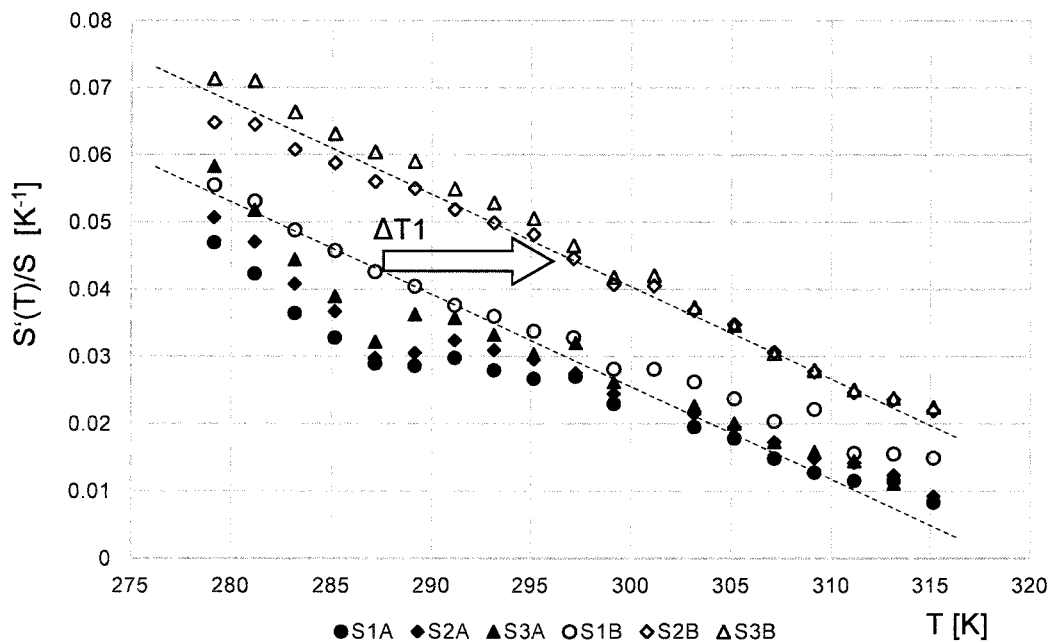

The application of the above-mentioned model for the assessment of electrochemical sensors is shown in FIG. 4. For GOx based electrochemical glucose sensors as described further above, the signal current is measured for different temperatures between 4° C. (277.15 K) and 42° C. (315.15 K), under operative conditions in a sodium azide stabilized physiological test solution (0.095 w % sodium azide, approx. 15 μM), having a glucose concentration of $c_{Glu} = 480$ mg/dl.

The used glucose concentration is well above the normal range of blood glucose values for healthy individuals (72-140 mg/dl). Measurements at a higher glucose concentration allows to increase the signal to noise ratio, which is particularly advantageous for the low signal currents at low temperatures. Furthermore a higher glucose concentration leads to a proportionally higher permeation rate of glucose through the membrane and thus a higher local glucose concentration at the detecting layer, which decreases the difference between active enzyme concentration and local glucose concentration at the detecting layer, thereby amplifying the influence of the enzyme activity on the sensitivity by reducing the effective reaction rate $k_c$, compared to physiological glucose concentration values.

For the experiments, the temperature of the prepared measurement setup is increased from 37° C. to 42° C., and then is decreased stepwise by increments of 1 K, keeping the temperature constant for each step for 12 minutes.

The experiment has been carried out for six different sensors: Sensor S1A is an unaltered, newly manufactured sensor, which has been swelled in test solution for one day at 37° C., prior to starting the temperature sweep experiment. Sensor S2A is equivalent to sensor S1A, but has been subjected to a heat treatment, resulting in the denaturation of a large part of the enzyme modules, with only 20% of active enzyme molecules left, as has been confirmed by corresponding measurements of the content of remaining active enzyme in the detecting layer. Like sensor S1A, it has been swelled in test solution for one day at 37° C. prior to the measurement. For sensor S3A, the concentration of enzyme in the manganese dioxide paste applied to the conductive layer during the manufacturing process, which later forms the detecting layer, had been reduced to 20% of the nominal concentration, resulting in a sensor similar to sensor S1A but only with 20% of its active enzyme. Like sensor S1A, it has been swelled in test solution for one day at 37° C. prior to the temperature sweep experiment. Sensors S2A and S3A serve as a well-defined test model for sensors with reduced enzyme activity that shall be assessed with the method according to the invention.

Sensors S1B, S2B, and S3B are identical to sensors S1A, S2A, and S3A, respectively. However, after having been swelled in test solution for one day at 37° C., and prior to carrying out the temperature sweep experiment, said sensors S1B, S2B, S3B have been subjected to 19 days of continuous operative conditions at 37° C. This means that said sensors have been actively measuring a glucose concentration during this period, which is equivalent to a sensor having been used by a patient during the suggested service life time when implanted in the subcutaneous tissue of the patient.

In the following, sensors S1A, S2A, S3A will be called "unstrained sensors", and sensors S1B, S2B, S3B will be called "strained sensors".

It can be expected that the loss in enzyme activity after a 19 day service period, which is the result of an unavoidable ongoing enzyme decay under operative conditions, will have more prominent effects for sensors S2B, S3B than for sensor S1B, since they already start with a considerably reduced enzyme activity.

The measured signal current I plotted against temperature T is shown in FIG. 4(*a*). For analysing the data based on the first approach, the sensitivity S is determined based on the measured signal current and the known glucose concentration of the test solution, as shown in FIG. 4(*b*). The calculated relative gradient $S'/S = (dS/dT)/S$ is plotted in FIG. 4(*c*).

The signal current decreases considerably over the temperature sweep (in the given experimental data by a factor of about 2.5-3). A measurement error $\Delta S$ of sensitivity S, being proportional to a measurement error $\Delta I$ of signal current I, will be more significant in the corresponding relative derivative $S'(T)/S$ for lower temperatures, since $\Delta(S'/S) = (\Delta S/S)^2$. Thus for 6° C. the signal to noise ratio in (S'/S) is 6.25-9 times higher than for 42° C. As can be seen in FIG. 4(c), the differences between the measured values for sensors S2A and S3A, as well as for sensors S2B and S3B, which should essentially be zero, are larger for lower temperatures than for higher temperatures.

As one can see in FIG. 4(c); the curve of a certain strained sensor S1B, S2B, S3B is shifted to higher temperatures, compared to the corresponding unstrained sensor S1A, S2A, S3A. Based on the function model explained further above, this corresponds to a positive shift $\Delta T_1$ of the transition temperature. This effect was to be expected, since GOx enzyme partially deteriorates during the 19 day operative service period, which decreases the effective catalytic reaction rate k. While for the unstrained sensors the visible effect of a reduction of the overall enzyme rate from 100% (S1A) to 20% (S2A, S3A) is small, an effect becomes clearly visible for strained sensors (S1B vs. S2B, S3B).

As predicted by the model, a similar effect can be seen between unstrained sensor S1A, having 100% of nominal enzyme concentration, and unstrained sensors S2A, S3A, both having 20% of nominal enzyme concentration, and thus having a reduced effective catalytic reaction rate $k_c$.

Surprisingly, it was found that the transition temperature shift effect is considerably larger between strained sensor S1B with nominal enzyme content and sensors S2B, S3B with 20% of nominal enzyme content, than between unstrained sensor S1A and unstrained sensors S2A, S3A. Without wishing to be bound to any theory, applicants believe that any difference in enzyme activity between sensors to be tested (represented here by S2A, 3A/S2B, S3B) and an ideal sensor representing the norm (represented here by S1A/S1B) gets considerably increased by straining the sensors prior to the temperature sweep experiment. Based on the measurement data in FIG. 4(c) it seems that the decrease in enzyme activity in a norm sensor after a 19 day service period (comparison of transition temperature shift between S1A and S1B) is considerably larger than 80% (comparison of transition temperature shift between sensors S1A and S2A, S3A).

This reduction factor, applied to a sensor with initially reduced enzyme activity, results in a multiplication of the involved reduction factors. If e.g. a service period of 19 days reduces the amount of active enzyme in a sensor to 10% of the original value, this will result for a norm sensor in a remaining enzyme activity of 10%. For a sensor for which the initial enzyme content is only 20% of the nominal value, e.g. due to a manufacturing problem or due to long-term storage, the remaining enzyme activity will be 2% of the nominal value.

In order to explain a possible quantitative assessment of the obtained experimental data, in FIG. 4(c) the data curve for sensor S1B and the data curves for sensors S2B, S3B have been approximated by two linear functions with identical gradient (dashed lines). The horizontal shift of the two linear functions is $\Delta T_1 \cong 11$ K, while the gradient is $[S''/S]_{measured} \cong -1.4*10^{-3}$. Using the formulas developed further above, it results a lower limit of the ratio between $p_c$ and $p_d$, namely $p_c/p_d \geq \exp[2(-[S''/S]_{measured})^{1/2}]) \cong 1.077$, and an upper limit for the ratio of the effective catalytic reaction rate of sensors S2B, S3B and sensor S1B:

$$k_{c,S2B,S3B}/k_{c,S1B} \leq \exp(-2\Delta T_1\{-[S''/S]_{measured}\}^{1/2}) \cong 0.44$$

Using the linear approximations for calculating the lowest and highest (S'/S), it results a difference $(S'/S)_{max}-(S'/S)_{min} \cong 0.065$, which again provides an upper limit of $$k_{c,S2B,S3B}/k_{c,S1B} \leq \exp[-\Delta T_1\{(S'/S)_{max}-(S'/S)_{min}\}] \cong 0.49.$$

Figure 5:
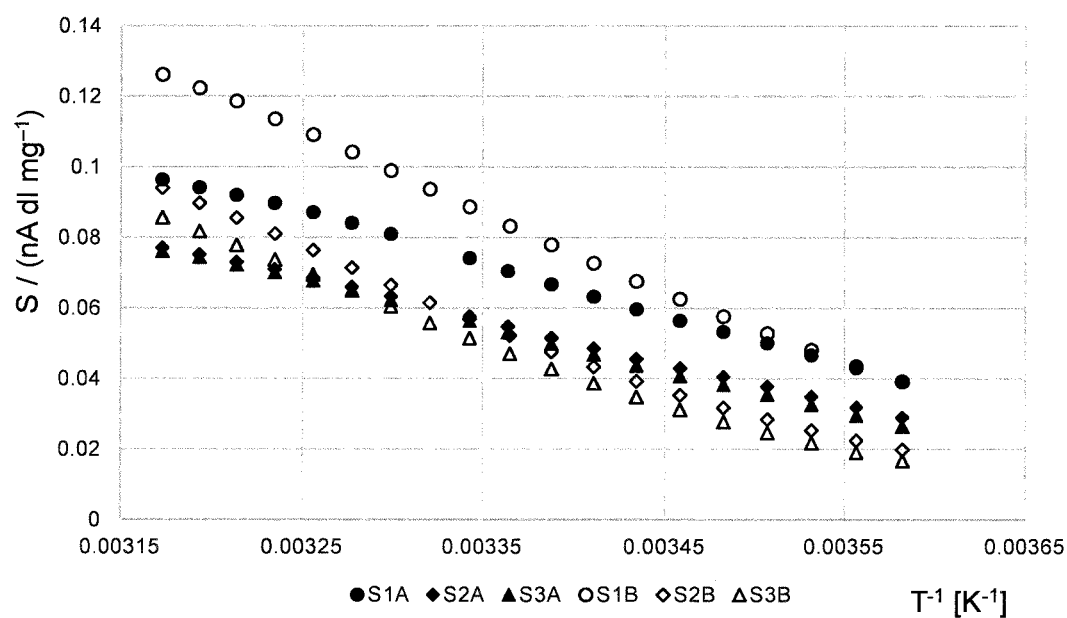
FIG. 5 shows experimental results of measurements of electrochemical glucose sensors, with (a) the sensitivity S vs. the inverse temperature 1/T, and (b) the relative derivative (dS/d(1/T))/S of the sensitivity vs. inverse temperature 1/T.
Figure 5:
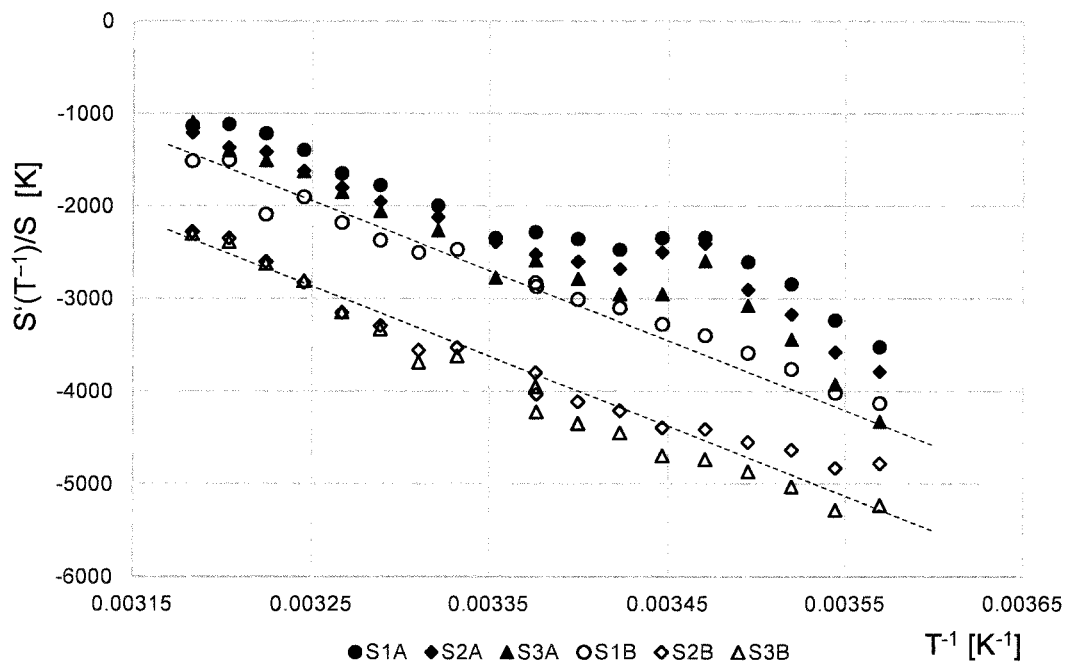

Similar to the first approach, a relative derivative of the sensitivity can derived based on the second approach, as a function of the inverse temperature $T^{-1}$ instead of temperature T. The experimental sensitivity data as shown in FIG. 4(b) plotted against the inverse temperature 1/T are shown in FIG. 5(a), while FIG. 5(b) shows the relative gradient $(dS/d(T^{-1}))/S$ as a function of $T^{-1}$.

In an application of the inventive method for testing the active enzyme content of newly manufactured sensors, a sample of sensors of a given manufacturing batch will be subject to the treatment as described above, comprising a preparatory swelling period in the test solution, and a subsequent period of constant operation under normal operative conditions. The operative condition time period may be 19 days, in order to emulate the maximum operative life time of a sensor, or shorter, or even longer. After this sample preparation, the signal current will be measured as a function of the temperature, and one of the two above-mentioned approaches will be used for analysing the relative derivative of the sensitivity.

For improving data accuracy, the temperature increments may be chosen smaller, thus providing more data points during a temperature sweep. Furthermore, in order to increase the signal-to-noise ratio, the very low signal currents during a temperature step can either be electronically integrated, or can be averaged in a digital signal processor.

It is also possible to apply a continuous temperature sweep, as long as the change in temperature is slow enough to avoid lag effects.

For the kinetic effect, it is irrelevant if the temperature is increased or decreased during the sweep.

In yet another approach, the temperature can be modulated, $T(t)=T_0+\Delta T \sin(\omega t)$, resulting in a modulated sensitivity $S(t)=S_0+\Delta S \sin(\omega t)$. For small temperature modulation amplitudes $\Delta T$ the sensitivity modulation amplitude $\Delta S$ will be proportional to the derivative dS/dT, while the sensitivity $S_0$ is given by the averaged modulated sensitivity signal. The relative derivative of sensitivity is directly accessible for a given temperature $T_0$ as by as $S'(T)/S=\Delta S/S_0$. In addition to directly obtaining the required derivative, this approach has the advantage of reducing the signal to noise ratio, which generally decreases with increasing signal frequency. Furthermore, such a temperature modulation will allow continuous measurements of both the sensitivity and its derivative for longer time periods at a constant temperature.

For assessing the outcome of a measurement, the resulting S'/S curve can be compared to a predefined target range that corresponds to a sensor with nominal enzyme activity values.

If calibration measurements with sensors of known reduced enzyme activity are available (as for example for sensors S2A, S3A), the measured curve S'/S may also be evaluated quantitatively, for example by determining a transition temperature shift of the curve and looking up the corresponding active enzyme concentration in the calibration table.

In an advantageous variant, the temperature sweep experiment will be carried out more than once, at different moments during the continuous operating conditions period. For example may the constant operation mode be interrupted every 3 days, and a temperature sweep experiment can be carried out. After the experiment, the temperature will return to normal operative conditions until the next temperature sweep takes place. Such an approach allows to monitor the change of the S'/S curve over time, which will provide additional information.

Instead of carrying out a temperature sweep over the complete range, it is also possible to carry out the temperature sweep over a comparably short range, e.g. between 36 and 38° C. While the resulting S'/S curve will generally be too short for determining a horizontal (temperature) shift of the curve, it will be possible to determine a vertical shift, or an increase of S'/S for a given temperature in regard to a nominal value, respectively, which in combination with a corresponding calibration table will also allow to assess the enzyme activity. Since a temperature sweep over a short range around the physiological temperature of the operative conditions can be carried out in less time than a sweep over the complete range, such an approach is particularly useful for repeated measurements during an operative condition period, as described above.

Surprisingly, applicants have found that measurements with azide stabilized physiological glucose test solutions result in higher sensitivities than with corresponding glucose test solutions without azide. For example lies the sensitivity of an S1B sensor between 0.040 at 6° C. and 0.126 at 42° C. for an azide stabilized glucose test solution (0.095 w % sodium azide, approx. 15 µM), as used in FIG. 4(b). For a similar glucose test solution without azide and 466 mg/dl glucose concentration the sensitivity lies between 0.008 at 6° C. and 0.028 at 42° C. (see FIG. 6, solution C2).

While the resulting S'/S values lie in the same range for both solutions, as has to be expected, the increased sensitivity (in the above-mentioned example by a factor of about 5) has a very advantageous effect on the signal-to-noise ratio of S'/S.

Without wishing to be bound to any specific theory, applicants believe that the increased sensitivity is the result either of an increased turnover of the redox reaction of hydrogen peroxide with manganese dioxide due the presence of azide ions, or the inhibition of parasitic hydrogen peroxide reduction paths that reduce the amount of hydrogen peroxide available for the primary reduction reaction. Such reactions can be the result of resulting from enzymatically catalysed reactions of impurities of other enzymes used in the manufacturing of GOx.

Variation of Glucose Concentration

A further approach to obtain information on enzyme activity is observing the dependency of the S'/S curve for different concentrations of glucose. As explained further above, for cases where the active enzyme concentration is not far above the local glucose concentration, the effective catalytic reaction rate will depend on the active enzyme concentration, and therefore on enzyme activity. For a given enzyme activity, a variation of the glucose concentration may lead to change in the effective catalytic reaction rate, which may result in an observable change in the S'/S curve.

Figure 6:
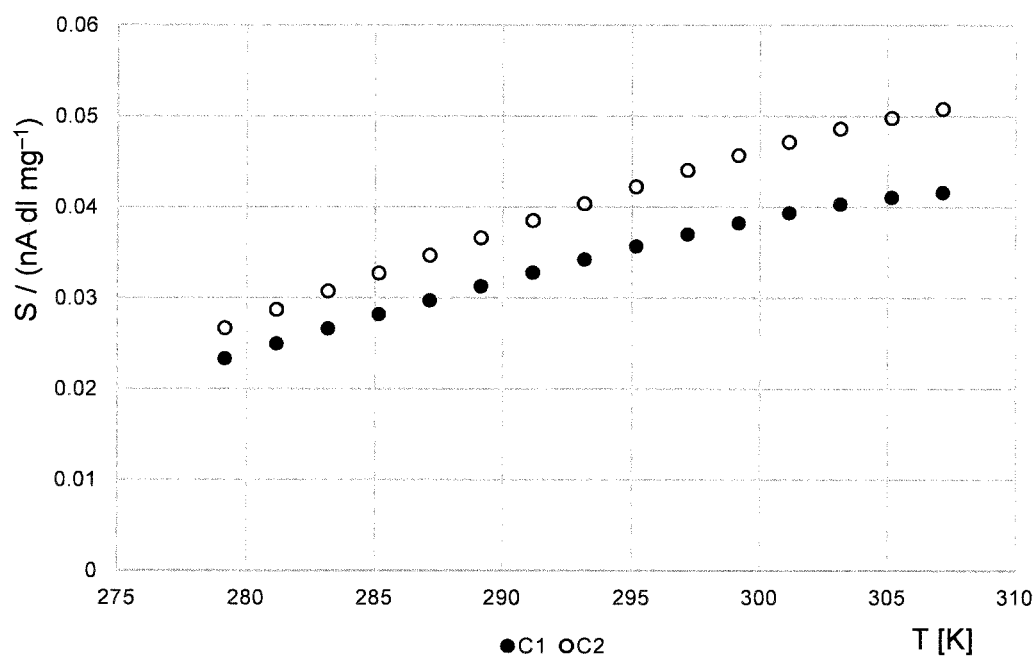
FIG. 6 shows (a) the experimentally determined sensitivity S of a sensor, as a function of the temperature, for two test solutions with different glucose concentrations; and (b) the corresponding relative derivative (dS/dT)/S of the sensitivity.
Figure 6:
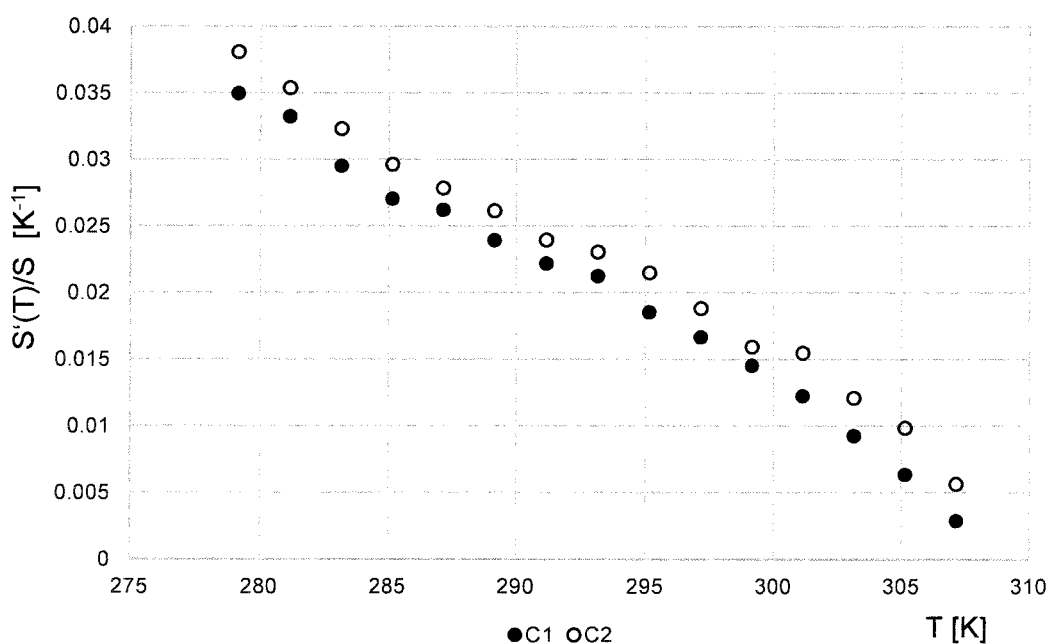

FIG. 6 shows the sensitivity S and relative derivative of sensitivity S'(T)/S of an unstrained sensor S1A for two test solutions with different glucose concentrations, measured as a function of the temperature, after pre-swelling for one day.

For each solution, the results of two sensors have been averaged. The test solutions did not contain azide. Test solution C1: glucose concentration 233 mg/dl. Test solution C2: glucose concentration 466 mg/dl.

As can be seen in FIG. 6(a), the increase of the glucose concentration by a factor 2 from solution C1 to solution C2 leads to an increase of the sensitivity. However, looking at the sensitivity alone does not allow to obtain more information. The S'/S curve in FIG. 6(b), on the other hand, shows a positive shift of the transition temperature, as it could be expected based on the model as used above, of about 2 K. This transition temperature shift is the result of a decreased effective catalytic reaction rate resulting from a decreased difference between active enzyme concentration and glucose concentration.

Thus it is shown that the variation of the glucose concentration can provide valuable additional information on the effective catalytic reaction rate, and thus on enzyme activity. Particularly the dependence of the effective catalytic reaction rate on the glucose concentration allows to discriminate between the influence of changes in enzyme activity and the influence of the diffusion rate, which may also change due to irreversible processes in the semipermeable membrane. Further below, an example of a decrease of the diffusion rate and its effect on the S'/S curve will be discussed (see FIG. 7).

Advantageously, the experiments are carried out for more than two different concentrations, covering a broad range of concentration values.

In a simple approach, the transition temperature shift is determined as a function the glucose concentration. Alternatively the combined S'/S curves will provide a data set that describes a surface above the temperature axis and the glucose concentration axis. This will allow an even more elaborate assessment of enzyme activity of a given sensor.

In an advantageous experimental setup, the change between different glucose concentrations is automatized.

Instead of carrying out a full temperature sweep, a sweep over a small temperature range can be used instead, and/or temperature modulation, as described further above.

Influence of Storage Temperature

One common approach for emulating the effects of long storage periods on certain devices in shorter time periods is storing said devices at increased temperatures.

For example may a GOx based electrochemical sensor as discussed above, with normal enzyme concentration, be stored at an increased temperature, e.g. 45° C., in order to simulate the effect of a longer storage period on the stability of the sensor under normal conditions at room temperature, thereby considerably reducing the amount of time necessary for such tests. At the same time, such increased temperature periods may be used to assess shipping stability, since during shipping the environmental temperature may increase to such temperature ranges for several days. Particularly the higher storage temperature will lead to an accelerated thermal deterioration of the enzyme in the dry state, and thus to a decrease in enzyme activity.

Figure 7:
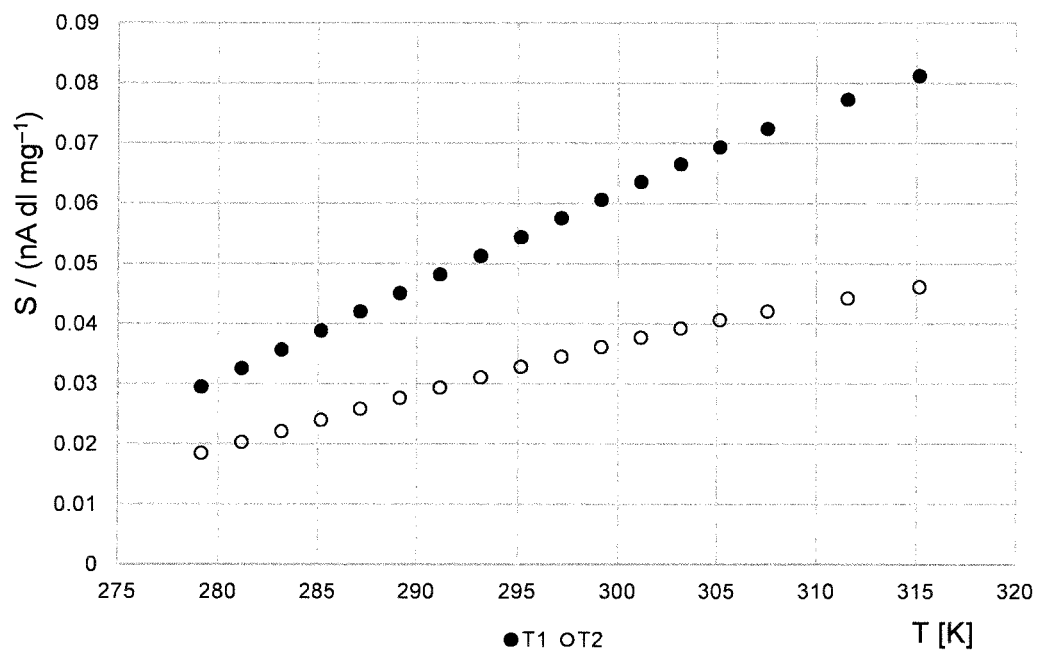
FIG. 7 shows (a) the experimentally determined sensitivity S of a sensor, as a function of the temperature, for two sensors stored under different conditions; and (b) the corresponding relative derivative (dS/dT)/S of the sensitivity.
Figure 7:
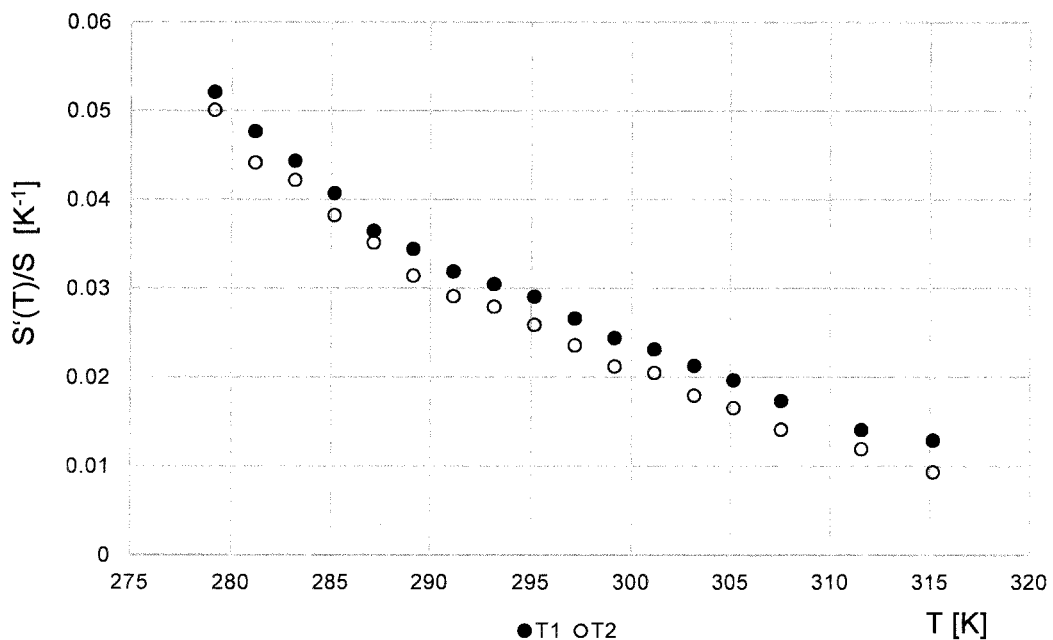

In FIG. 7, two sensors of the same production batch with nominal enzyme content were stored after manufacture at two different temperatures. One such sensor was stored at room temperature (data set T1). Another, identical sensor was stored for 3 days at 45° C. (data set T2), which is a typical setup for a shipping stability test. After pre-swelling for one day, the sensitivity was measured as a function of the temperature, with the same test solution as for FIG. 4.

As can be seen in FIG. 7(a), the sensor stored at 45° C. shows a sensitivity that is about half of the sensitivity of the sensor stored under normal conditions. A decrease of the sensitivity is known for such storage tests, and is known to be partially caused by a thermal deterioration of the semipermeable membrane, which leads to a decrease of permeability for glucose, and thus to a decreased local concentration of glucose at the detecting layer, which directly leads to a decrease in the resulting signal current for a given glucose concentration. At the same time, said reduced local glucose concentration counteracts the effect of increased enzyme deterioration during storage at increased temperature, and thus reduced enzyme concentration: The relative difference between enzyme concentration and glucose concentration is larger than it would be with unchanged membrane permeability, and the sensor sensitivity stays longer in the linear range.

Although the data for sensor S1A are partially noisy in regard to the S'/S curve in FIG. 7(b), it can be seen that both storage conditions lead to a positive shift of the transition temperature. However, storage under increased temperature actually leads to a smaller positive shift of the transition temperature, compared to normal storage conditions, instead of a larger positive transition temperature shift as it could be expected from a further decreased enzyme activity compared to normal storage conditions, and contrary to the sensitivity data as such. This effect can be explained by the mathematical model. Assuming a case where the effective catalytic reaction rate $k_c^*$ is decreased (due to a reduced enzyme activity), and the diffusion rate $k_d^*$ is also decreased (due to a reduced glucose permeability of the deteriorated membrane), the transition temperature shift can be calculated as $$\Delta T_1 = T_1^* - T_1 = -\ln(k_{c0}^*/k_{d0})/\ln(p_c/p_d) + \ln(k_{c0}/k_{d0})/\ln(p_c/p_d)$$
$$= -\ln(k_{c0}^*/k_{c0})/\ln(p_c/p_d).$$

Thus a decrease in the diffusion rate leads to negative transition temperature shift, while a decrease in the effective catalytic reaction rate leads to a positive transition temperature shift.

In the case of the two sensors of FIG. 7, the transition temperature of sensor T2 is lower than for sensor T1, corresponding to a negative $\Delta T_1$, which means that the ratio of the diffusion rates $k_{d,T2}/k_{d,T1}$ is smaller than the ratio of the effective catalytic reaction rates $k_{c,T2}/k_{c,T1}$. Qualitatively spoken, higher storage temperatures lead to a more dominant effect of membrane deterioration that starts to cover the effect of enzyme denaturation.

Nevertheless it will be possible to distinguish the two effects, by carrying out the sensitivity measurement with test solutions having different glucose concentrations, as explained above with FIG. 6. Since the effective catalytic reaction rate decreases with an increased glucose concentration, while the diffusion rate will not be influenced by the glucose concentration as long as viscosity does not get too high, a positive transition temperature shift will result for a series of increasing glucose concentrations. Using a suitable kinetic model, and fitting the output of the model to the measured data, it will then be possible to determine both the enzyme activity and the membrane characteristics. This will allow to use increased temperatures for storage tests, thereby shortening the required time for long-term stability tests.

Another approach for differentiating between the effects of enzyme activity and diffusion rate comprises the measurement of the S'/S curve after different storage periods. For example, starting with a large set of sensors, at certain intervals one or more of the sensors will be removed and the sensitivity will be measured as a function of the temperature The resulting S'/S curves will allow to determine the transition temperature shift as a function of the storage period. Alternatively the S'/S data can be plotted against the temperature axis and the storage time.

Alternatively or in addition, other experimental parameters may be varied that have an influence on the effective catalytic reaction rate. For example may the sensitivity vs. temperature curve be obtained for different pH values. Since the pH value has an influence on the enzyme activity, the effective catalytic reaction rate will depend on the pH value. The range of pH values is limited by the stability of the electrode under such conditions, particularly the stability of the enzyme and the semi-permeable membrane. GOx enzyme is active in the pH range of 4-7, with an optimum value at 5.5.

Another possibility is the measurement of the sensitivity vs. temperature curve for different partial pressures of oxygen. Depleting the experimental setup from available molecular oxygen will decrease the effective catalytic reaction rate, since oxygen is a co-reactant for the enzymatic oxidation of glucose.

In a further approach to modulate the enzyme activity, thereby obtaining more information on the two effects influencing the sensitivity, test solutions with different amounts of enzyme inhibitors may be used, in order to artificially reduce the turnover of the enzyme, and thus the effective catalytic reaction rate. For GOx enzyme, inhibitors such as $Ag^+$, $Hg^{2+}$, and $Cu^{2+}$ ions may be used as inhibitors, or phenylmercuric acetate (CAS No. 62-38-4) and (4-Carboxyphenyl)chloromercury (CAS 59-85-8).

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

LIST OF REFERENCE NUMERALS 1 working electrode
2 insulating carrier substrate
3 conductive layer
4 detecting layer
4a active area of working electrode layer
5 semi-permeable membrane
6 analyte solution, body fluid

The invention claimed is:

1. A method for testing an enzyme based electrochemical sensor, wherein the sensor is for quantitative detection of analytes in aqueous solutions, comprising:
providing an electrochemical sensor having a working electrode and a counter electrode, the working electrode comprising an electrical conductor, a solid-state matrix being electrically connected with said conductor and containing an immobilized enzyme able to catalytically convert a primary analyte into a secondary analyte that can be oxidized or reduced when a suitable potential is applied at the working electrode, and a membrane covering said matrix and separating it from the outside, said membrane being permeable for the primary analyte, such that primary analyte molecules present in an aqueous solution with which the working electrode is in contact can pass through the membrane to the matrix, where the primary analyte molecules can be catalytically converted into second analyte molecules;
providing a measurement setup operatively coupled to the electrochemical sensor and providing output signals of the electrochemical sensor;
contacting the electrochemical sensor with a test solution comprising a concentration of the primary analyte;

subjecting the electrochemical sensor to a swept range of temperature values T;

measuring output signals Z for different temperature values T;

determining derivatives Z' of the output signals Z as functions of temperature T or inverse temperature 1/T;

determining relative derivatives as the ratios Z'/Z at different temperatures T, or inverse temperatures 1/T;

determining a transition temperature shift based on the relative derivatives Z'/Z; and testing said electrochemical sensor based on the determined transition temperature shift.

2. The method according to claim 1, wherein an offset function $Z_{offset}$, is subtracted from output signal Z prior to using output signal Z for determining the derivative Z'.

3. The method according to claim 2, wherein the offset function $Z_{offset}$ is determined in an iterative process with at least one iteration round, said iterative process comprising the assessment of a derivative Z' and/or relative derivative Z'/Z obtained using a certain offset function, and determining changes in the offset function based on said assessment of the derivative and/or relative derivative.

4. The method according to claim 1, wherein the enzyme is glucose oxidase, the primary analyte is D-glucose, and the secondary analyte is hydrogen peroxide.

5. The method according to claim 1, wherein the swept range of temperature values is increased or decreased stepwise.

6. The method according to claim 1, wherein the temperature is swept in a range between 2° C. and 42° C.

7. The method according to claim 1, wherein the applied temperature is modulated with an offset temperature, frequency and amplitude, resulting in a modulated output signal with an offset and modulation amplitude; and the relative derivatives Z'/Z are determined as the quotients of output signal modulation amplitude and output signal offset.

8. The method according to claim 1, wherein the obtained relative derivate Z'/Z values are compared to corresponding calibration data sets corresponding to sensors comprising a range of amounts of active enzyme.

9. The method according to claim 1, wherein the testing comprises determining if a function fitted to the relative derivate Z'/Z data reaches a certain value.

10. The method according to claim 9, wherein the determined temperature shift is compared to calibration data including transition temperature shift data corresponding to sensors comprising a range of amounts of active enzyme.

11. The method according to claim 1, wherein the sensor is subjected to a certain treatment prior to measuring the output signals by at least one of the group consisting of: subjecting the sensor to a certain temperature for a certain time period, and subjecting the sensor to operative conditions for a certain time period.

12. The method according to claim 1, wherein after measuring the output signals, said sensor is subjected to a certain treatment prior to carrying out another measurement by subjecting the sensor to a certain temperature for a certain time period; or subjecting the sensor to operative conditions for a certain time period.

13. The method according to claim 1, wherein the measurement is carried out with two or more test solutions having different properties selected from the group consisting of different concentrations of the primary analyte, different properties of enzyme inhibiting agents, and different pH values.

* * * * *